United States Patent [19]

Mader et al.

[11] 3,975,727
[45] Aug. 17, 1976

[54] AUTOMATED CALIBRATION AND STANDARDIZATION APPARATUS

[75] Inventors: Arthur H. Mader, Mount Vernon; Donatas V. Gasiunas, Carmel; Edward W. Stark, Garden City, all of N.Y.

[73] Assignee: Technicon Instruments Corporation, Tarrytown, N.Y.

[22] Filed: June 28, 1974

[21] Appl. No.: 484,027

[52] U.S. Cl. .................... 340/347 NT; 73/61.1 C; 356/205; 340/347 CC
[51] Int. Cl.² ........................................ H03K 13/02
[58] Field of Search ........................... 356/179–182, 356/205; 340/347 NT, 347 AD, 347 CC; 235/197, 151.3; 73/61.1 C

[56] References Cited
UNITED STATES PATENTS

| | | | |
|---|---|---|---|
| 3,241,432 | 3/1966 | Skeggs et al. ...................... | 356/179 |
| 3,349,390 | 10/1967 | Glassman ...................... | 340/347 AD |
| 3,568,181 | 3/1971 | Weaver ...................... | 340/347 AD |
| 3,662,163 | 5/1972 | Miller et al. ...................... | 235/197 |
| 3,681,577 | 8/1972 | Gasiunas ...................... | 235/151.3 |
| 3,685,048 | 8/1972 | Pincus ...................... | 340/347 AD |
| 3,686,665 | 8/1972 | Elias et al. ...................... | 340/347 AD |
| 3,701,145 | 10/1972 | Bergin ...................... | 340/347 NT |
| 3,824,585 | 7/1974 | Meijer ...................... | 340/347 NT |

*Primary Examiner*—Thomas J. Sloyan
*Attorney, Agent, or Firm*—S. P. Tedesco; Stephen E. Rockwell

[57] ABSTRACT

New and improved apparatus is provided for the calibration and standardization of the analog output signal level of automated analysis equipment, which level varies as a function of the concentration of the constituent being analyzed. Such apparatus comprises an A/D converter including a dual-slope integrator for translating the output signal level to a time interval which varies as a function of the constituent. Such apparatus further includes means for generating the inverse function of the analytical function, which is applied to linearize and scale the output signal level and to convert such level directly to digital form. Also, provision is made for the calibration and standardization, on an individual basis, of each of a plurality of analytical channels in a multi-channel system.

25 Claims, 10 Drawing Figures

AUTOMATED CALIBRATION AND STANDARDIZATION APPARATUS

BACKGROUND OF THE INVENTION

1. Field of the Invention

This invention relates to automated apparatus for the calibration (standardization) of automated analytical equipment, wherein the analytical results are linearized with respect to the particular constituent being analyzed, the analytical measure of the constituent being nonlinear.

2. Description of the Prior Art

The prior art is replete with automated systems for the automated analysis of materials. Generally, these materials are in the liquid form, and are introduced into the apparatus as a continuous stream of successive samples. For example, one such apparatus is described in U.S. Pat. No. 3,241,432, issued to L. T. Skeggs and assigned to a common assignee. Such apparatus is operative to react each of the successive samples, in turn, and present such samples, in turn, to an analytical portion. Often the analysis is effected colorimetrically, the reaction of the sample producing a color product having an optical density which varies as a non-linear function of the concentration of the particular constituent under analysis. In colorimetric analysis, the output signal varies exponentially (antilogarithmically) with the concentration of the constituent, according to Beer's Law, as hereinafter discussed. Accordingly, to obtain meaningful analysis, the non-linear output signal of a colorimeter must be linearized by apparatus having a logarithmic input-ouput characteristic such that the reported analytical results vary linearly with the concentration of the constituent.

Also, analysis can be effected by the use of ion-selective electrodes, wherein the output signal varies logarithmically with the concentration of the constituent, according to the Nernst equation, as hereinafter discussed. In this case, the non-linear (electrode) output signal must be linearized by apparatus having an antilogarithmic input-output characteristic to effect linearization.

Besides linearization, it is essential that the analytical system be calibrated, according to the particular analysis to be effected, by proper relationship to a standard, i.e., a test sample of known concentration. Such calibration in prior art analytical systems required the manual adjustment of the system by the operator, which is not only time-consuming but introduces a source of human error. The more advanced analytical systems have sought to exclude or, at least, to minimize the intercession of the human operator within the "control loop" of the system. As can be appreciated, improper calibration of the system would produce inaccurate results which, for example, in the field of public health, could be disastrous. Elimination of the human operator, therefore, would reduce the possibility of error in the analytical results and, also, increase overall efficiency of the system.

Techniques have been proposed for the automatic calibration and standardization of analytical systems, which have succeeded in substantially eliminating the human operator from the control loop. Also, such techniques allow for a continuing or frequent calibration of the apparatus, to provide accurate operation in the presence of drift. One such automated system has been disclosed in U.S. Pat. No. 3,681,577 to D. V. Gasiunas and assigned to a common assignee. This prior art system, however, is particularly operative to calibrate and standardize automatically those analytical systems having a response which varies linearly with the concentration of the constituent, for example, as is the case in spectroscopic analysis. Such system, however, is not particularly suitable in non-linear systems. Structurally, such system comprises an analog-digital processing system (including an A/D converter) wherein background-noise is translated to an equivalent DC signal and subtracted automatically from each of the analytical signals developed. Additionally, a variable gain is introduced into the processing system, the particular gain corresponding to the concentration range of signals under analysis, to amplify each analytical signal to an appropriate level for proper processing. The prior art signal processing system operates strictly on a linear basis. Fundamentally, such processing system is calibrated via a single standardization point (after subtraction of background) with respect to standards for each of the constituents and a digital scale factor is introduced to operate on each converted signal, so as to produce system results properly scaled in concentration units.

OBJECTS OF THE INVENTION

It is an object of this invention to provide new and improved apparatus for the automatic calibration of analytical systems.

It is a further object of this invention to provide new and improved apparatus for the automatic calibration, linearization, and the analog-to-digital (A/D) conversion for analytical systems, wherein the analytical signal varies non-linearly, e.g., exponentially, logarithmically, etc., as a function of the concentration of the constituent under analysis.

It is another object of this invention to provide a fully automated apparatus, operative in closed-loop fashion, to linearize a non-linear analytical system.

It is a further object of this invention to provide new and improved apparatus for the calibration and standardization of analytical systems, and which is capable of compensating automatically for any base-line drift occuring in the system, for example, chemical interferences; drift in light intensity, etc.

SUMMARY OF THE INVENTION

The present invention provides a unified apparatus for A/D conversion and the automatic calibration and standardization of non-linear systems, for example, as described in the above-identified Skeggs et al patent, by compensating the output thereof with a particular non-linear function which is generated internally. During the initial calibration cycle, the signal-processing system is calibrated automatically to generate and store a scale factor tending to proportion the output derived from each analytical channel. This compensating factor, initially, is derived according to the response of the corresponding analytical channel during the calibration cycle, i.e., with respect to a standard. Preferably, to effect two-point calibration of an individual analytical channel, a low-calibration or baseline cycle and a high-calibration cycle, operative typically on low-concentration and high-concentration standards, respectively, are performed. The latter cycle, in time, effects comparisons with concentration units of both standards stored within the processing system. The response of the processing system to the second standard introduced automatically determines a digital scale factor which controls a non-linear compensator to linearly scale the analytical results. Apropos of colorimetry, the low-concentration standard usually is water, providing 100% transmission or zero optical density, and the high-concentration standard is of any known value, e.g. 70% transmission. In the case of colorimetry, the response of the signal processing apparatus to the low-concentration and high-concentration standards results in the generation of binary numbers (words) proportional to baseline and scale factor, respectively. In the case of systems employing ion specific electrodes, such response results in the generation of binary numbers proportional to baseline and the logarithm of the scale factor. These binary numbers are stored and retained in memory, in order to provide certain internal controls for the measurement of samples having unknown concentration.

In colorimetric analysis, equal increments in concentration of a particular constituent produce equal factors of change in the output energy level, e.g., photodiode current which is converted to a voltage signal. Accordingly, the amplitude of the output voltage signal varies as an exponential (antilogarithmic) function of the concentration of a particular constituent, according to Beer's Law. The colorimeter output signal, whether derived from a standard or sample, is translated, by appropriate A/D conversion circuitry, such that changes in amplitude are converted into proportional time intervals. An important feature of this invention is the proper weighting of increments in the voltage signal by counting (integrating) a varying frequency during the time intervals, such that the frequency variations provide the proper weighting. This weighting is achieved by the use of a hyperbolic sweep-frequency generator. The sweep pattern of the sweep-frequency generator is modified (scaled) according to the response of the system to the high-concentration standard. The scaled output of the sweep-frequency generator is gated appropriately, so as to accumulate output pulses therefrom during a time interval proportional to the difference in the percentage transmission, e.g. %T, between low-concentration standard and that of the sample being measured. Such accumulated count is added automatically to the value of the low-concentration standard to obtain a valid analytical result. Since the change in %T between the low-concentration standard and the sample concentration varies non-linearly with concentration, the accumulated count of pulses generated by the sweep-frequency generator, which have been appropriately scaled, effectively linearizes and proportions the analytical results with respect to concentration. Additionally, the analytical results are also linear with respect to optical density, which is defined in logarithmic terms since concentration units and O.D. units are proportional to each other. It should be appreciated that the integral of a hyperbolic function, that is, the accumulation of pulses from the hyperbolic sweep frequency generator, is a logarithmic function, and provides the basis of the linearization of exponentially varying signals.

In the case of compensating a logarithmic response, as when ion-selective techniques are employed, the hyperbolic sweep-frequency generator is not used. Rather, the frequency sweeping is effected, for example, in the form of an exponential sweep, since the integral, i.e., the accumulated counts, is an exponential (antilogarithmic) function, whereby the logarithmically-varying characteristic of the electrode is linearized.

An additional feature of the invention is the automatic compensation for drift in the apparatus. In colorimetric techniques, it is desirable to provide a corresponding "blank" channel which serves as a ready reference to indicate system drift. Drift can arise from lamp intensity variation or chemical "interference" both of which alter baseline. The "blank" sample is of known concentration, usually 100% transmission. Appropriate circuitry is provided to modify the signal processing within the apparatus, so as to maintain constant the time interval during which output pulses of the sweep-frequency generator are counted for a particular concentration, regardless of drift. In electrode techniques, drift is a function of alteration in the output voltage of the electrodes within the apparatus, such that compensation may be achieved by reintroduction of the first calibration standard in order to update the baseline word.

With regard to colorimeter techniques, the invention finds application also with inverse-color reactions, i.e., color is removed and percentage transmission (%T) of light through the flow cell increases with increasing concentrations of the constituent, as well as with normal reactions where color increases and %T decreases with increasing concentration of the constituent.

DESCRIPTION OF THE PREFERRED EMBODIMENT

Figure 2:
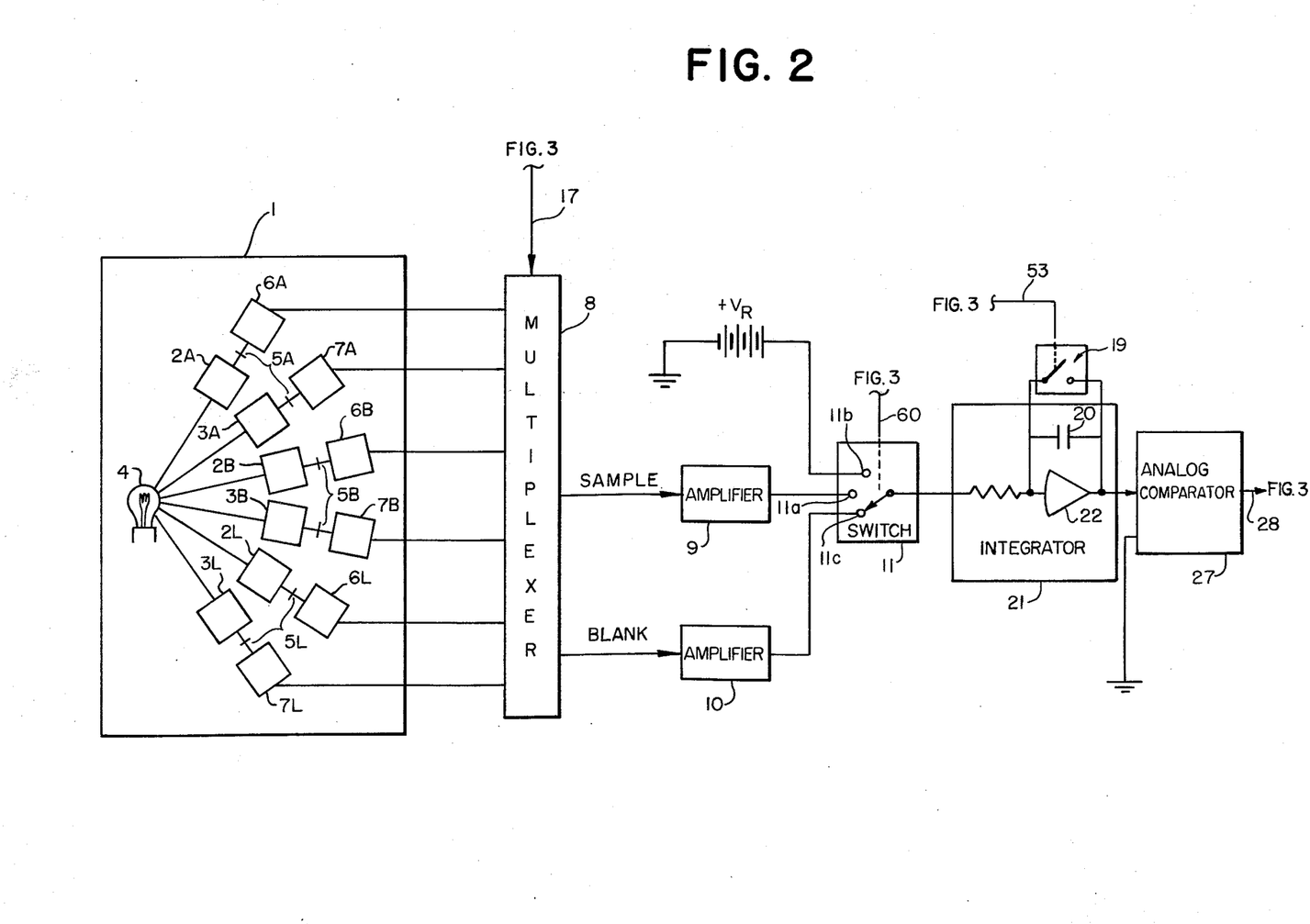
FIGS. 2, 3 and 4 are block diagrams of a preferred system embodying the present invention.
Figure 3:
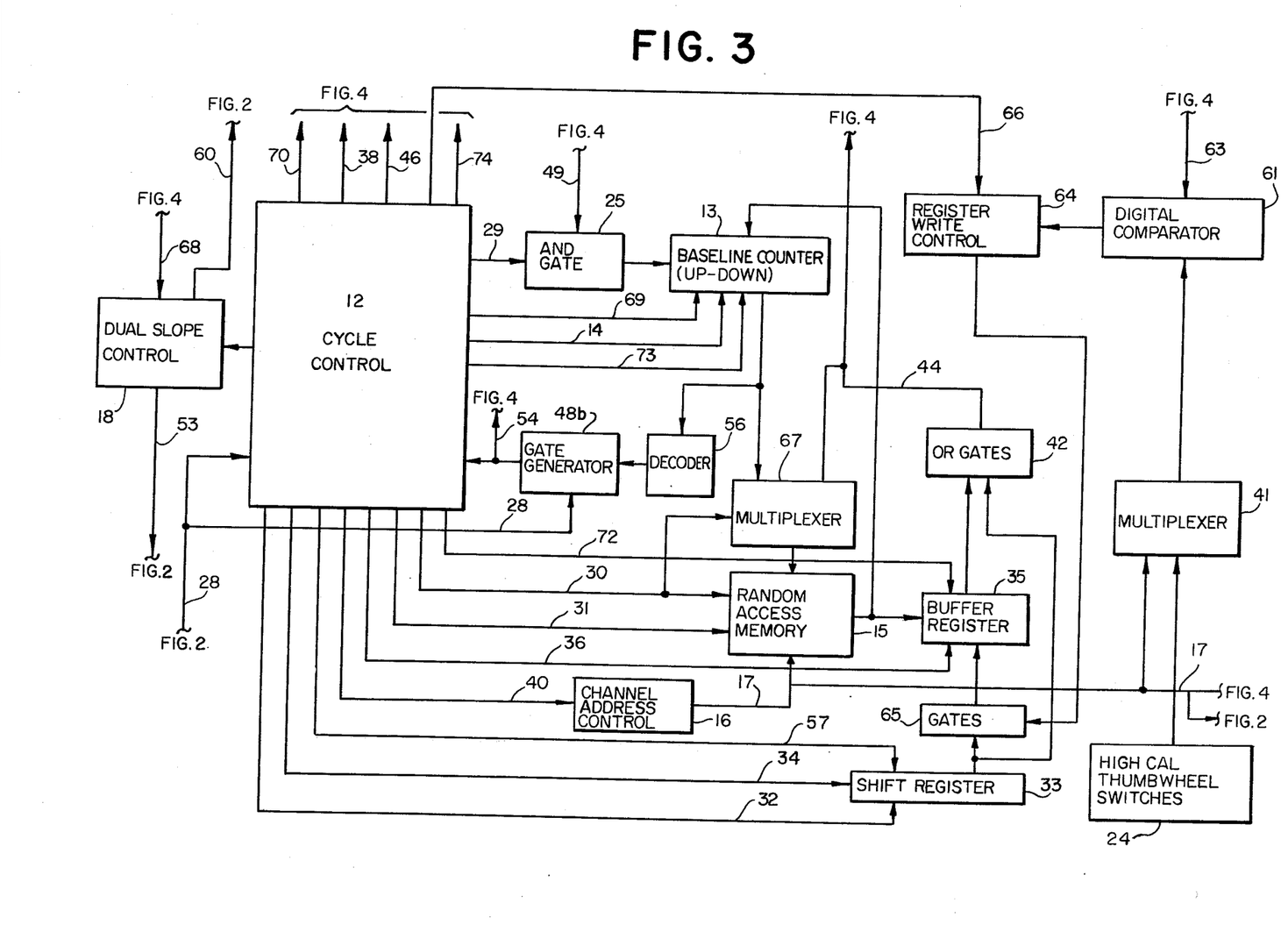
Figure 4:
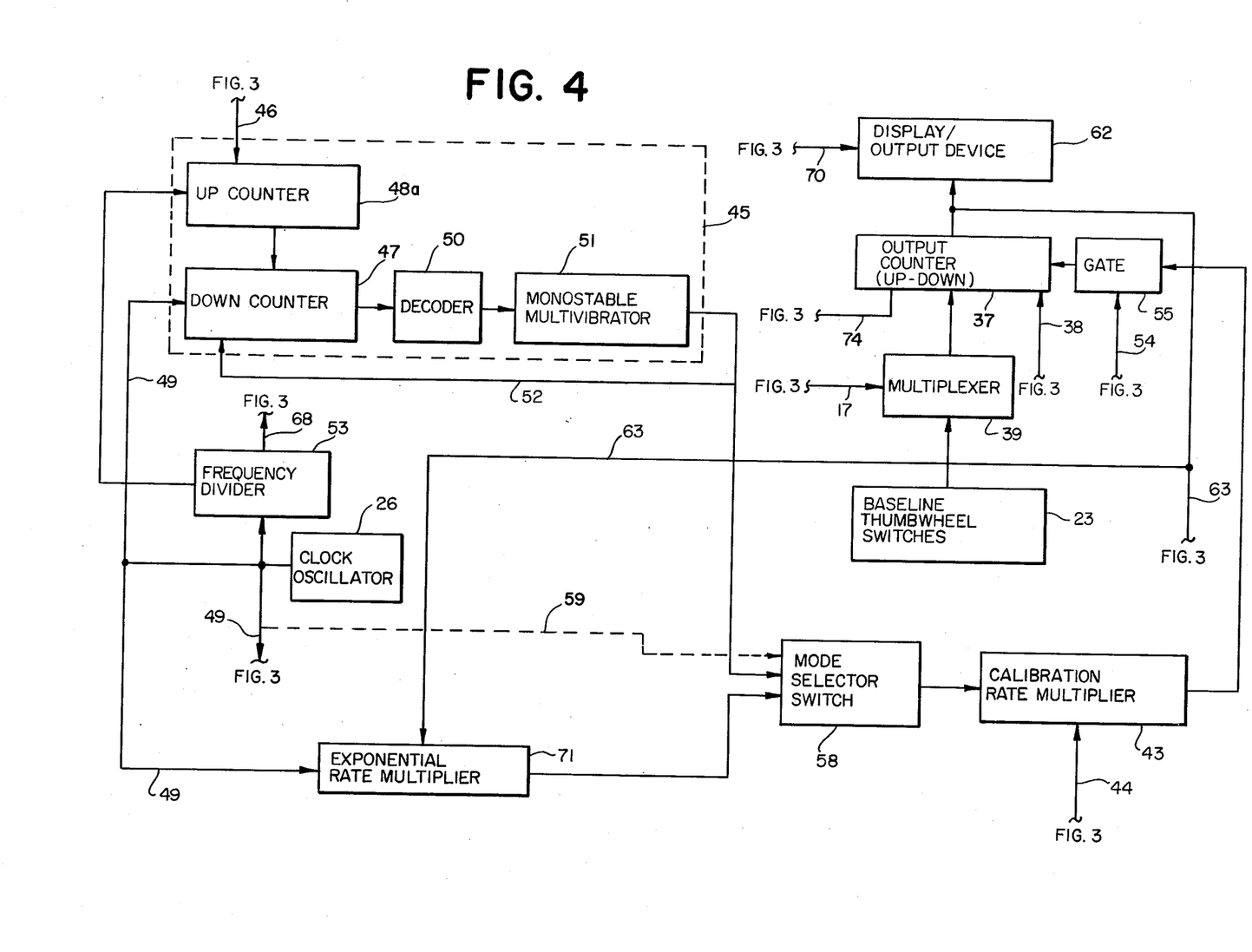

An automated analytical system for example, as shown and described in U.S. Pat. No. 3,241,432, is schematically indicated in FIGS. 2–4. Such analytical system comprises a plurality of sample flow cells 2A, 2B–2L, having associated therewith "blank" flow cells 3A, 3B–3L, respectively. Blank standards associated with the particular analyses being performed in the associated sample flow cells 2A, 2B–2L are passed concurrently through the corresponding blank flow cells, 3A, 3B–3L. As described in U.S. Pat. No. 3,241,432, aliquots of successive liquid samples, are reacted for the testing of a particular constituent, and passed successively and in proper phased relationship through sample flow cells 2A–2L, respectively, and colorimetrically analyzed by known techniques. Each sample flow cell 2A–2L corresponds to a particular methodology being performed. The reaction of the sample aliquots passed through each sample flow cell produces a color reaction having a percentage transmission %T, which varies non-linearly as a function of the concentration of the particular constituent, according to Beer's Law. A light source 4 illuminates each of the sample flow cells 2A–2L and blank flow cells 3A–3L, the light incident on each flow cell being appropriately filtered by optical filters 5A–5L, respectively, to effect the analysis at appropriate wavelengths. The light transmitted through sample flow cells 2A–2L and blank flow cells 3A–3L and filters 5A–5L is detected by photodetectors 6A–6L and 7A–7L, respectively. Photodetectors 6A–6L and 7A–7L are connected, in turn, through multiplexer 8 to preamplifiers 9 and 10. The series of electrical analog signals from preamplifier 9 is indicative of the respective concentrations of particular constituents being analyzed in the sample aliquots, each signal varying exponentially as a function of the respective concentration of the constituent according to Beer's law. As described in U.S. Pat. No. 3,241,432, these analytical signals of aliquots of a same sample are recorded in correlated fashion.

Figure 6A:
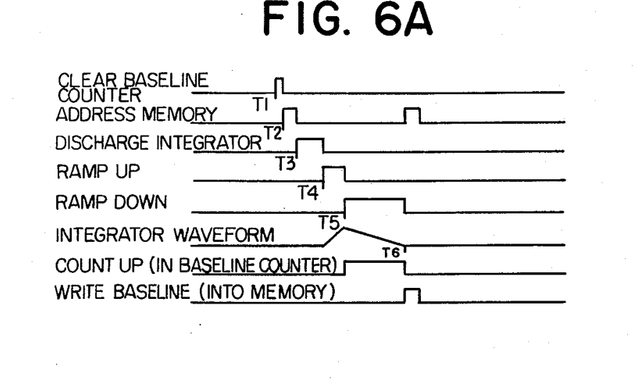
FIGS. 6A–6C are timing diagrams useful in understanding the present invention.

To linearize each such analog signal and directly obtain the concentration of the particular constituent in digital form, each signal is operated upon, in turn, by signal processing apparatus capable of effecting such conversion to linearized digital form. This A/D conversion is integral with linearization (and standardization) and converts non-linear analog inputs to linearized digital outputs without the necessity of producing either a linearized analog or a non-digital representation of the signal as an intermediate result. In effect, the signal processing apparatus is an A/D convertor having linearizing and standardizing capabilities. Such apparatus, however, must be initialy calibrated with respect to baseline and known standards, so as to generate the scaling compensation to be introduced. To effect such calibration, the operator initially sets low-cal, or baseline, thumbwheel switches in switch bank 23 (FIG. 4) and high-cal thumbwheel switches in switch bank 24 (FIG. 3) corresponding to each analytical channel. These thumbwheel switches are set, according to the assayed concentrations in the low-cal and high-cal standards, respectively, as references to which the system is to be calibrated. To effect the low-cal calibration, the operator introduces the low-cal standard into apparatus 1, and sets mode selector switch 58 according to the particular type of compensation to be effected, e.g., logarithmic or exponential compensation, and initiates the operation of the cycle control 12, to sequence the low-cal calibration cycle. At time T1 (FIG. 6A), cycle control 12 commences the low-cal cycle by resetting baseline counter 13 along lead 14. Random access memory 15 is addressed at time T2 by channel address control 16 along lead 17; the information to be stored in memory 15, however, is not yet available, so that this constitutes an optional step which can be omitted, if desired. For example, if cycle control 12 is event-sequentially organized, it is convenient to retain the memory address step, since it is a subset of steps depicted in FIG. 6C, which in turn is a subset of the timing steps indicated in FIG. 6B. However, in alternate forms of implementing cycle control 12, it is usually convenient to eliminate the step.

Figure 1A:
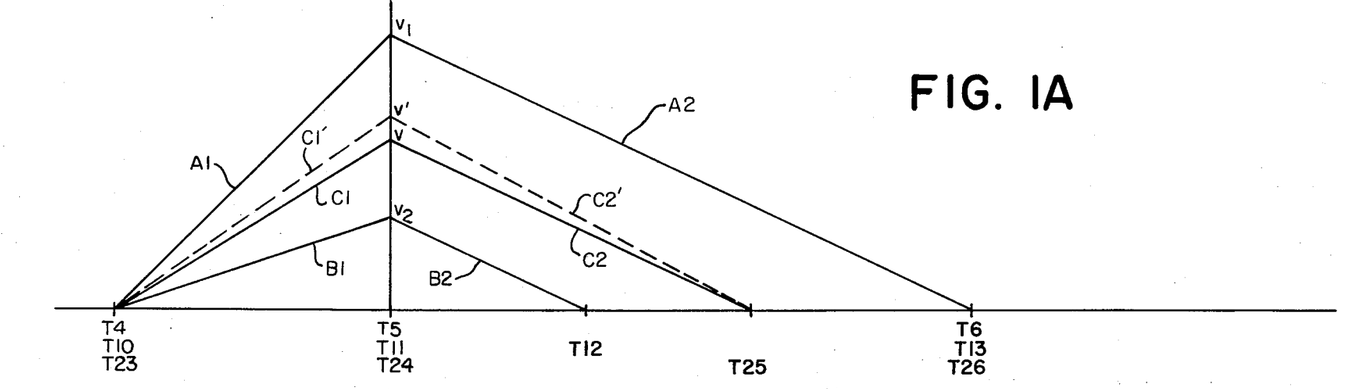
FIG. 1A is a timing diagram for the A/D conversion function performed by the present invention.

At time T3, dual slope control 18 momentarily operates switch 19 along line 53 to discharge the integrating capacitor 20 of integrator 21. At time T4, and assuming that integrator 21 has been discharged and a standard of known low-concentration, e.g. $H_2O$, is passing through sample flow cells 2A–2L, switch 11 is controlled by dual slope control 18 along line 60 to connect the output of sample preamplifier 9 via switch 11a to integrator 21. Integrator 21 comprises a capacitor 20 connected across an operational amplifier 22, as shown in FIG. 2. The particular function of integrator 21 is to translate the electrical analog voltage signal generated by each of the photodetectors 6A–6L, in turn, and amplified by sample preamplifier 9 into an equivalent time duration, as illustrated in FIG. 1A. The charging rate of capacitor 20, indicated by the slope of line A1 in FIG. 1A, is a function of the analog voltage from sample preamplifier 9. Since the ramp-up period, times T4–T5, is a constant during both calibration and measurement cycles of the individual analytical channels, the accumulated charge on capacitor 20 is a function of the optical density of the aliquot, whether sample or standard, present in the particular flow cell 6 being viewed. The ramp-up period is timed by an asynchronous counter, not shown, in dual slope control 18, which receives a 50 kHz frequency input from frequency divider 53 along line 68. Since the characteristics of the output from corresponding photodetector 6A are non-linear, the accumulated charge on capacitor 20 varies non-linearly with respect to the concentration of the constituent in the aliquot present in the flow cell being viewed. As indicated in FIG. 1A, the accumulated charge on capacitor 20 reaches a magnitude V1, during the ramp-up period T4–T5.

At time T5, dual slope control 18 operates switch 11 to connect the input of integrator 21 to a fixed reference potential $V_R$ along contact 11b. The discharge of the capacitor 20 between time intervals T5–T6, or ramp-down period, is illustrated in the timing diagram by line A2, the rate of discharge being proportional to the magnitude of $V_R$. Accordingly, the duration of the ramp-down period T5–T6 is proportional to the magnitude of the accumulated charge, which is proportional to V1.

An indication of the baseline or low-cal standard has been introduced by the operator into the baseline thumbwheel switches 23. To convert the baseline voltage V1, corresponding to 100%T through sample flow cell 2A, to a time duration, cycle control 12 instructs baseline counter 13 via line 73 to count up and enables gate 25 at time T5 to pass the 5 mHz signal from oscillator 26 along line 49 to the input of baseline counter 13. As capacitor 20 of integrator 21 is discharging at a rate proportional to a fixed reference voltage $V_R$, the slope of line A2 of FIG. 1A is constant, regardless of the magnitude of the accumulated charge at time T5 on capacitor 20. As capacitor 20 discharges, as indicated by line A2, baseline counter 13 counts up at a fixed 5 mHz rate.

As illustrated, the output of integrator 21 is connected to the input of the analog comparator 27, which is referenced to ground. When capacitor 20 is discharged to ground potential, comparator 27 generates an output to cycle control 12 along line 28, indicative of "base-line cross-over" at time T6. Cycle control 12 inhibits gate 25 along line 29, so as to stop baseline counter 13 from counting. Accordingly, the count accumulated in baseline counter 13 during ramp-down period T5–T6 is proportional to the voltage $V_1$ on capacitor 20, which, in turn, is proportional to the analog voltage supplied from photodetectors 6A. Ramp-down period T5–T6 defines a time reference against which the ramp-down periods (time durations) of the analytical signals can be compared. Concurrently, at time T6, cycle control 12 provides appropriate word address and write inputs, respectively, along lines 30 and 31 to store the accumulated count in baseline counter 13 within the memory 15 via multiplexer 67 at the channel address corresponding to the analytical channel being calibrated, as identified by channel address control 16 along line 17.

The operation, as described, is repeated for each of the analytical channels A–L in apparatus 1, the intensity of light transmitted through each of sample flow cells 2A–2L being detected by photodetectors 6A–6L, in turn. The particular baseline count for each analytical channels A–L, as accumulated by baseline counter 13, is stored in the appropriate address in memory 15. The result of the low-cal, or baseline, calibration operation is to reference the individual analytical channel to a corresponding baseline, i.e., 100%T, whereby each channel is compensated for signal level conditions peculiar thereto. A baseline word (time reference) is obtained for each of the analytical channels A–L, as described above, by addressing multiplexer 8 such that each photodetector 6A–6L is connected, in turn, to the integrator 20.

When the baseline, or low-cal, cycle has been completed for each of the analytical channels A–L of apparatus 1, the operator introduces a high-cal standard into apparatus 1, an indication of its concentration having been set in the high-cal thumbwheel switches 24.

During the high-cal cycle, the processing apparatus is calibrated by a successive-approximation algorithm with respect to a standard of known concentration, i.e., the high-cal standard, to determine the proper scale factor of the compensation to be introduced and, thereby, effect a two-point calibration of the system. The high-cal calibration cycle is effected subsequent to the baseline calibration, as described above, and the protocol of the calibration cycle is controlled by cycle control 12.

The sample flow cells 2A–2L are washed, e.g., by the passage therethrough of a wash liquid, following completion of the low-cal cycle and a high-cal standard is passed through each. At time T7, cycle control 12 operates channel address control 16 along line 17 to address multiplexers 39 and 41 and clears shift register 33 along line 34 and buffer register 35 along line 36. Concurrently, cycle control 12 presets output counter 37 along line 38 to load the settings of the baseline thumbwheel switches 23 via multiplexer 39 corresponding to the appropriate analytical channel, e.g., A, into output counter 37. The settings of high-cal thumbwheel switches 24 corresponding to the appropriate analytical channel, e.g., A, are applied to the input of digital comparator 61 through multiplexer 41, as controlled by channel control 16.

At time T7′, cycle control 12 presets the 16-position shift register 33 along line 32 with a "1" in its most significant position, i.e., 1000000000000000; concurrently, buffer register 35 is cleared along line 36 by cycle control 12. The outputs of corresponding positions in shift register 33 and buffer register 35 are connected to corresponding dual-input OR gates, included in block 42, whose outputs are connected to a calibration rate multiplier 43 along line 44. The information in shift register 33 is superimposed on the information stored in buffer register 35, to control the operation of the rate multiplier 43 in scaling the linearizing time function of frequency, as hereinafter described.

At time T8′, memory 15 is addressed along lines 30 to read out the baseline count corresponding to the appropriate analytical channel, e.g. A, generated during the low-cal cycle. Baseline counter 13 is preset by cycle control 12 along line 69 with appropriate baseline word stored in memory 15. Thus, the system is prepared to reconstruct the time gate T5–T6 during which the baseline count (word) was generated in response to introduction of the baseline standard.

At time T9, cycle control 12 operates switch 19, so as to discharge capacitor 20 and condition the integrator 21 for the first sub-cycle of high-cal calibration cycle. Concurrently, the high-cal standard (of known concentration) is passing through flow cell 2A–2L. At time T10, capacitor 20 has fully discharged and cycle control 12 operates switch 11 to connect the output of photodetector A, indicative of the light transmission through the first sample flow cell 2A, along contact 11a to integrator 21. During the ramp-up period T10–T11, capacitor 20 charges to $v_2$, i.e., the analog output of flow cell 2A, as indicated by line B1. At time T11, the ramp-up period of the high-cal cycle is completed; dual slope control 18 opens switch contact 11a and connects integrator 21 to the fixed reference potential $V_R$ via contact 11b. Since the ramp-up periods T4–T5 and T10–T11 during baseline and high-cal calibration cycles are of equal time duration, as indicated in FIG. 1A, the accumulated charges are proportional to %T, and the voltage proportional to such charges bear a known relationship to the respective concentrations of the standards by Beer's Law, as hereinafter more fully described.

Figure 1B:
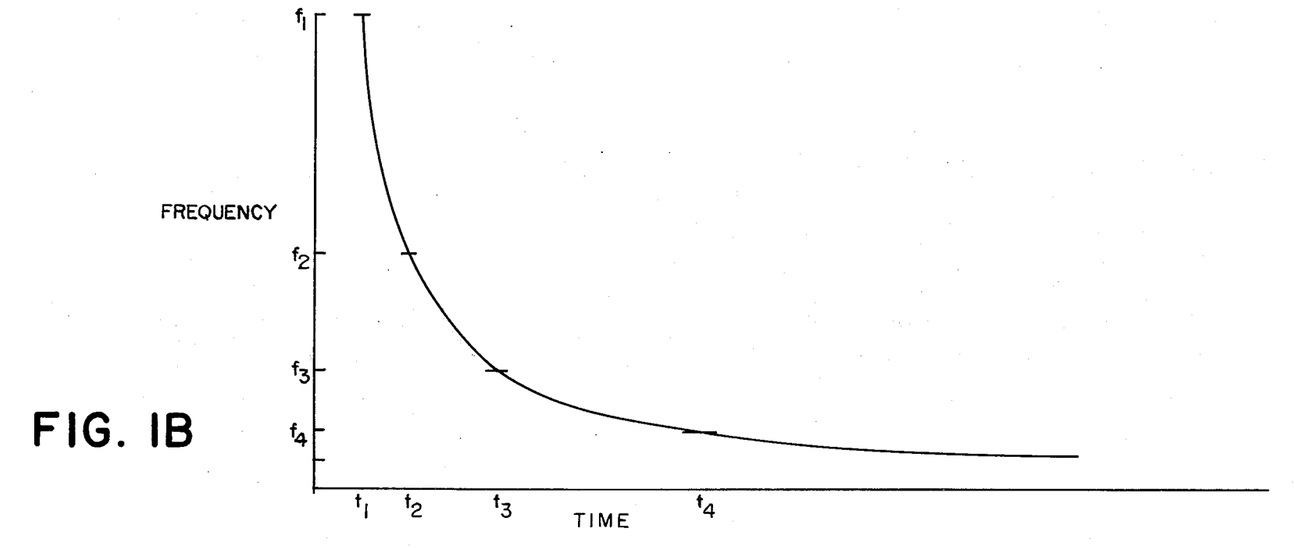
FIG. 1B depicts the frequency vs. time function of the hyperbolic sweep-frequency generator, used to effect linearization.

At time T11, the hyperbolic sweep-frequency generator 45 is reset along line 46. Sweep-frequency generator 45 operates to provide a pulse train whose frequency varies hyperbolically with time (inverse time function), as illustrated in FIG. 1B. The output of sweep-frequency generator 45 is directed, through the mode selection switch 58 to calibration rate multiplier 43, which scales the output of generator 45 according to the degree of scaling necessary to effect calibration. As illustrated, sweep-frequency generator 45 comprises a fast down-counter 47 connected to the output of a 5 mHz oscillator 26 along line 49 and a slow up-counter 48a connected to the output 1000:1 frequency divider 53, which divides down the 5 mHz signal generated by oscillator 26 to provide pulses at a 5 kHz rate to up-counter 48a. Also, the output of down-counter 47 is connected to a decoder 50, having an output connected to the input of monostable multivibrator 51. The output of the monostable multivibrator presets the down-counter 47 (with the content of the up-counter) upon its reaching the "zero" state, as determined by decoder 50. During operation, the number counted in the up-counter 48a is preset in down-counter 47, each time that down-counter 47 counts to "zero". The "zero" count state of down-counter 47 is detected by decoder 50, which triggers multivibrator 51 to preset the down-counter 47 along line 52 with the count in up-counter 48a. Additionally, each output pulse of multivibrator 51 is directed through mode selector switch 58 to calibration rate multiplier 43. Such output pulses have a variable frequency given by the expression $f_2/(f_1t)$, where $f_1$ and $f_2$ are 5 kHz and 5 mHz, respectively. Thus, the frequency generator 45 varies inversely with time, i.e., hyperbolically, such that the same number of pulses is generated within geometrically increasing time intervals as marked by $t_1, t_2, t_3, t_4$, etc., in FIG. 1B, where $t_1=Ct_2$; $t_2=Ct_3$; $t_3=Ct_4$; etc. and where C is a constant. Consequently, $f_1=f_2/C$; $f_2=f_3/C$; $f_3=f_4/C$; etc. As illustrated in FIG. 1B, the constant C has a value of 0.5, since linearly increasing concentration in a liquid sample, according to Beer's law, produces geometrically decreasing response in transmitted light intensity, integrator 21 operates to convert geometrically decreasing voltage into geometrically decreasing time duration. The latter is converted to linearly increasing concentration by counting in output counter 37 the output of hyperbolic frequency sweep generator 45 from the crossover of the output of integrator 21 until expiration of the time gate generated by baseline counter 13. Note: the transformation is from nonlinear analog to linear digital and is effected by virtue of the properties of a hyperbola, wherein equal areas reside above limits possessing the same ratio to each other. Finally, by scaling the frequency of the sweep-frequency generator 45 in the calibration rate multiplier 43, the total count N accumulated in output counter 37, as hereinafter described, indicates directly the concentration of the sample. During the calibration cycle, the output of calibration rate multiplier 43 and, hence, the output counter 37 are scaled, such that the latter equals the known concentration of the high-cal standard, indicated by the setting of high-cal thumbwheel switches 24 at the conclusion of the successive approximation algorithm.

Accordingly, at time T11 (FIG. 6B), cycle control 12 resets sweep-frequency generator 45 along line 46; instructs baseline counter 13 via line 73 to count down; and enables gate 25 to pass the 5 mHz pulses from oscillator 26 to baseline counter 13. Dual slope control 18 operates switch 11 to connect integrator 21 to fixed reference potential $+V_R$ via contact 11b. During the period T11-T13 of the high-cal calibration cycle, baseline counter 13 counts down from the baseline word recalled from memory 15 at time T8. As hereinafter described, the baseline word in baseline counter 13 provides a fixed time duration reference, i.e., corresponding to 100%T, for use during the high-cal cycle and subsequent measurement cycles. Such reference is the time required for baseline counter 13 to count down to zero. In normal colorimetric techniques, the crossover point of the high-cal cycle occurs sooner in time than the baseline crossover point, since the voltage in capacitor 20 is necessarily of lesser magnitude. Since capacitor 20, during ramp-down period T11-T12, is discharged by a current proportional to a fixed reference potential $V_R$, the discharge rate or slope of the ramp-down curve B2, is constant, i.e., the same as that of ramp-down curve A2. Accordingly, the crossover point for a particular concentration during the high-cal cycle, whether standard or sample, will occur after expiration of a time interval measured from the initiation of ramping down, I.E., at time T11, which interval is directly proportional to the percentage transmission of light energy (referenced to 100% at baseline) through the sample flow cell. The time interval between the crossover corresponding to the concentration of the constituent and the fixed time duration reference (marked at the point in time when baseline counter 13 counts to zero) is a function only of concentration change from baseline concentration, and is used to gate the scaled output of sweep-frequency generator 45 into output counter 37, which is preset with the baseline concentration by low-cal thumbwheel switches 23, in order to produce a number equal to the concentration of the high-cal standard.

To scale the frequency of sweep-frequency generator 45 in order to effect proper scaling of the frequency input to output counter 37, the count accumulated in output counter 37 during the time interval T12–T13 is compared against the setting of high-cal thumbwheel switches 24. To effect such comparison, the output of analog comparator 27 is connected along line 28 to gate generator 48b; the other input of gate generator 48b is connected to the output of decoder 56. The output of gate generator 48b is connected along line 54 to the control input of gate 55, which connects the output of rate multiplier 43 to output counter 37.

During the high-cal cycle, the output of output counter 37 is compared to the calibration standard concentration by successive approximations with scaling appropriate to the algorithm provided by calibration rate multiplier 43, until the content of the output counter 37 is equal to the setting of high-cal thumbwheel switches 24. During the first approximation, calibration rate multiplier 43 is controlled according to the state of shift register 33, set at time T7' to its most significant position. At time T11, cycle control 12 enables gate 25 along line 29 to decrement baseline counter 13 at the 5 mHz rate, i.e., the output of oscillator 26 directed along line 49. Concurrently, capacitor 20 of integrator 21 discharges, as indicated by the line B2 in FIG. 2, during time interval T11–T12 and baseline counter 13 begins to decrement at a 5 mHz rate. When capacitor 20 has discharged at time T12, indicating the high-cal crossover, analog comparator 27 enables gate generator 48b along line 28 which, in turn, enables gate 55 along line 54. Accordingly, the output of calibration rate multiplier 43 passes to output counter 37, which has been preset with the setting of baseline thumbwheel switches 23 at time T8. At calibration crossover at time T12, therefore, output counter 37, instructed by cycle control 12, via line 74, begins to count up at a variable rate, scaled by calibration rate multiplier 43, and baseline counter 13 continues to count down at the fixed 5 mHz rate. Such operation continues until such time as the baseline counter 13 counts to zero, as indicated at T13; decoder 56 responds to disable gate generator 48b, thereby inhibiting both gate 55 along line 54 and further incrementing of output counter 37. Under certain conditions of operation, e.g., when the concentration of the second calibration standard introduced into the system is lower than that of the first calibration standard, output counter 37 is instructed by cycle control 12 via line 74 to count down. Cycle control 12 is pre-programmed to permit counting up or counting down in output counter 37 during standardization according to the protocol of calibration for each of the analytical channels A–L.

As can be appreciated, the count in output counter 37 is the sum of the preset count and the integral of that portion of the curve of FIG. 1B corresponding to that time interval between the high-cal crossover at time T12 and baseline crossover at T13. To effect proper scaling, the count accumulated in output counter 37 during time interval T12–T13 should equal the difference between the respective settings of baseline thumbwheel switches 23 and high-cal thumbwheel switches 24. Such equality scales the output of the analytical channel, e.g., channel A, being calibrated.

As previously mentioned, high-cal thumbwheel switches 24 are connected through multiplexer 41 to one set of inputs to digital comparator 61. Also, output counter 37 is connected along line 63 to output display device 62 and to the reference inputs of digital comparator 61. The output of digital comparator 61 is connected to register write control 64, the output of which is connected to the enabling terminal of gates 65. At time T13, coincident with baseline counter 13 counting to zero, cycle control 12 operates register write control 64 along lead 66. In the event that the word stored in high-cal thumbwheel switches 24 is greater than the count appearing in output counter 37 at the conclusion of time interval T12–T13, digital comparator 61 operates register write control 64 to enable gates 65. When gates 65 are enabled, the "1" stored in shift register 33 is transferred and stored in the corresponding bit position in buffer register 35. In the event, however, that the count in output counter 37 is greater than the setting of high-cal thumbwheel switches 24, digital comparator 61 inhibits gates 65 via register write control 64 at time T13 and the "1" stored in shift register 33 is not transferred into the corresponding position in buffer register 35.

At time T14, cycle control 12 operates along line 57 to clock shift register 31, so as to transfer the "1" to the adjacent lower order bit position i.e., the second bit position, which count is superimposed on the contents of buffer register 35 to enable corresponding OR gates 42 to control calibration rate multiplier 43 and scale the output of sweep-frequency generator 45.

Figure 6B:
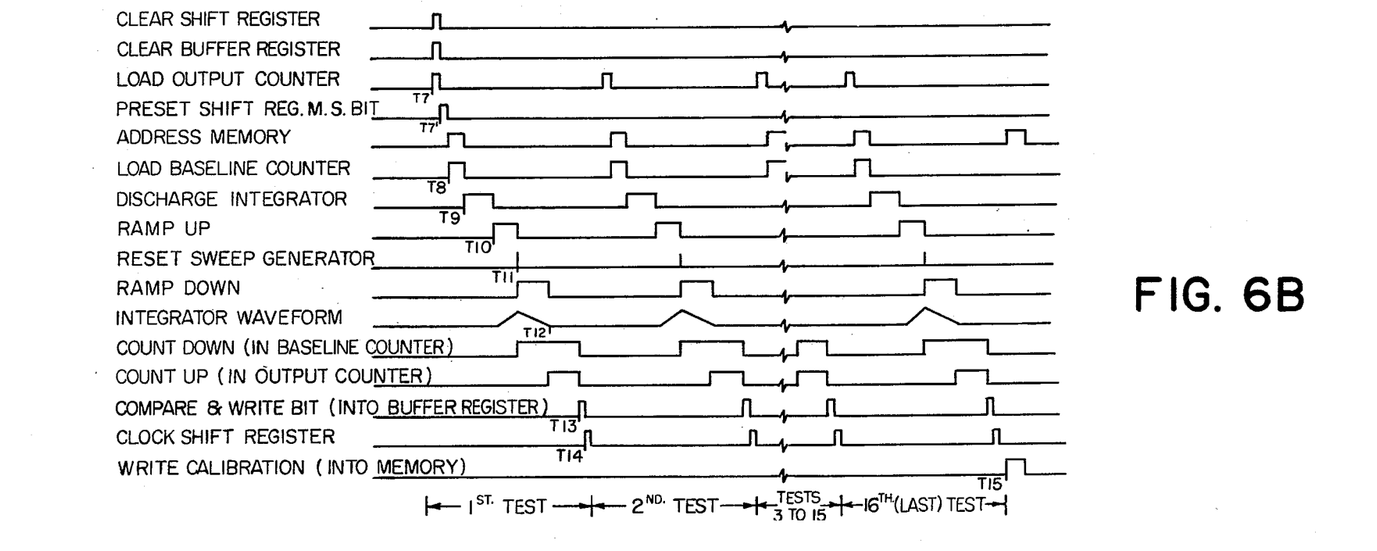

As illustrated the high-cal calibration is effected in 16 successive sub-cycles, as shown in the timing diagram of FIG. 6B. Accordingly, shift register 33 and buffer register 35 each contains 16 positions. The process, described above, is repeated 16 times, until the lowest frequency in calibration rate multiplier 43 has been tested, the information word in buffer register 35 being built up successively. Each calibration sub-cycle, in effect, tests the calibration word in buffer register 35 on which is superimposed the bit stored in shift register 33, in order to control calibration rate multiplier 43 by means of comparing the content of output counter 37 with the content of high-cal thumbwheel switches 24 set for the particular analytical channel. The successive calibration sub-cycles develop an information word in buffer register 35 which is a measure of the scaling factor necessary to proportion the frequency of the sweep-frequency generator 45, such that the count in output counter 37 equals the known concentration of the calibration standard, as indicated by the setting of high-cal thumbwheel switches 24. The information word thus developed in buffer register 35 at the completion of the sixteenth calibration sub-cycle is stored in memory 15 at time T15, as hereinafter described. Cycle control 12 operates channel address control 16 along line 40 and addresses multiplexer 67 along line 30 to store the calibration word at an appropriate address in memory 15, from which it can be recalled during subsequent measuring cycles.

The baseline and high-cal calibration cycles, hereinabove described, are completed for each of the analytical channels A–L, in turn, whereby a baseline information word and a calibration information word are stored at appropriate word and channel addresses in memory 15. Calibration of the processing apparatus is completed prior to the actual analysis of the samples. At the completion of the baseline and high-cal calibration cycles, each off flow cells 2A–2L is appropriately washed and, subsequently, corresponding sample aliquots derived from single liquid sample to be analyzed are appropriately reacted and passed through each of flow cells 2A–2L in appropriate phase relationship, as described in the above U.S. Pat. No. 3,421,432.

At time T20, as a sample aliquot is passing through the first flow cell 2A, cycle control 12 operates channel address control 16 along line 40 to address multiplexer 39 along line 17 to permit loading of baseline data stored in high-cal thumbwheel switches 23 and corresponding to flow cell 2A into output counter 37, as enabled by preset line 38. At time T21, cycle control 12 enables alternately lines 69 and 72 to load the calibration and baseline words, corresponding to flow cell 2A and previously stored in memory 15, into baseline counter 13 and buffer register 35, respectively. This is accomplished by providing alternating calibration and baseline word addresses along line 30. Accordingly, the processing apparatus, which is time-shared by the various analytical channels A–L, is controlled by these recalled information words which respectively control slope and zero of the output from counter 37. A different set of words is recalled for each channel.

As the sample aliquot passes through first flow cell 2A at time T22, dual slope control 18 operates switch 19 along line 53 to discharge capacitor 20. When capacitor 20 has been discharged, at time T23, dual slope control 18 operates switch 11 along line 60 to connect integrator 21 to the output of the photodetector 6A associated with the first flow cell 2A along contact 11a.

During the timed ramp-up period, i.e., time interval T23–T24, which is of equal duration as the ramp-up periods during the baseline and high-cal calibration cycles, capacitor 20 of integrator 21 charges along C1 of FIG. 1A at a rate proportional to the intensity of the light transmitted through the sample flow-cell 2A and incident on photodetector 6A. At the completion of the ramp-up period, at time T24, the voltage v across capacitor 20 is, according to Beer's law, a non-linear function of the concentration of the constituent under analysis.

Figure 5A:
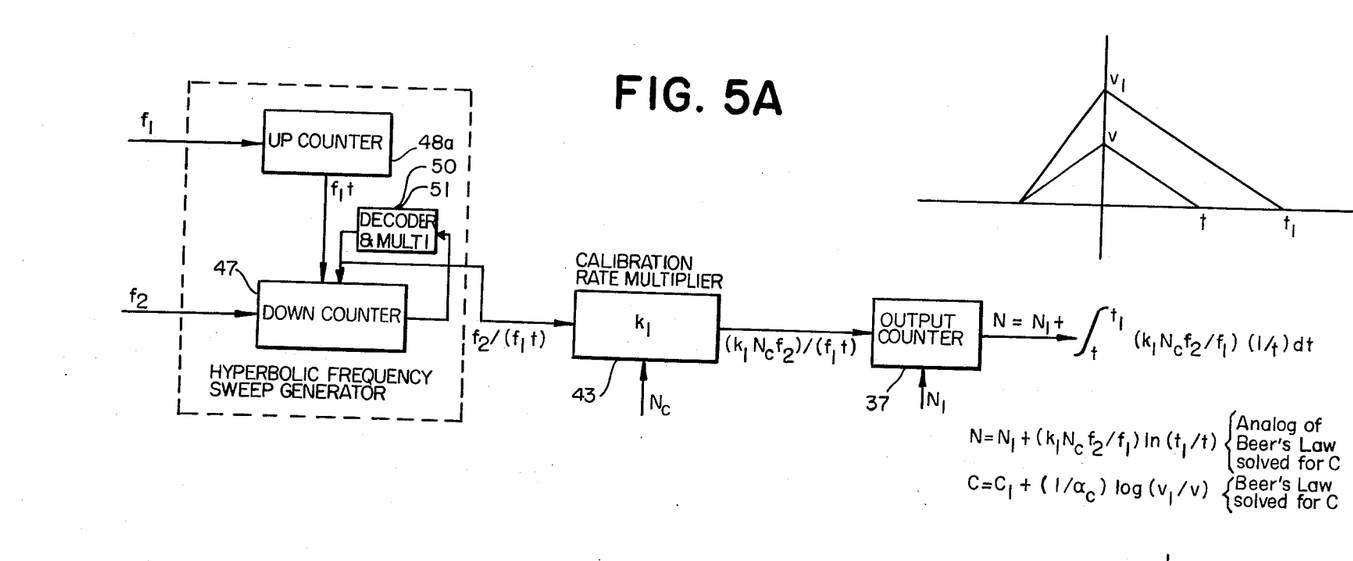
FIG. 5 is a mathematical model of the signal processing apparatus of the present invention.

At the completion of the ramp-up period at time T24, cycle control 12 operates (1) to reset the sweep-frequency generator 45, (2) to enable gate 25 along line 29 to pass the 5 mHz signal from oscillator 26 to baseline counter 13, and (3) to operate switch 11 to connect integrator 21 to the fixed reference potential $V_R$, so as to initiate the ramp-down period. As capacitor 20 is discharged, baseline counter 13 is decremented at the 5mHz rate and, concurrently, the sweep-frequency generator 45 begins its non-linear sweep; however, output counter 37 is not counting, since gate 55 is inhibited. When capacitor 20 has discharged, at time T25 along C2 of FIG. 1A, comparator 27 operates to enable gate generator 48b along line 28 which, in turn, enables the gate 55 along line 54. Output counter 37 commences to count up (or count down) from the preset baseline information, as contained in the baseline thumbwheel switches 23 at a non-linear rate. The average rate at which output counter 37 counts is determined by the duration of the ramp-down period, since sweep-frequency generator 45 is continuously sweeping since time T24 and, also, the scaling factor introduced into calibration rate multiplier 43, according to the calibration word clocked into buffer register 35, at time T21. At time T25, baseline counter 13 is continuing to count down at a fixed rate, while output counter 37 starts counting up at a variable rate, appropriately scaled. Output counter 37 continues to count until such time that baseline counter 13 counts to zero, at time T26, and decoder 56 disables gate generator 48, to inhibit both gate 55, along lead 54, and further counting in output counter 37. The count present in output counter 37, therefore, is the summation of the number of pulses accumulated during time interval T25–T26, i.e., the difference between the respective ramp-down periods (time durations) of the low-cal, or baseline cycle and the measure cycle, and the number which was preset initially into output counter 37. The difference between such ramp-down periods is proportional to the voltage difference, i.e., $v_1-v$ with respect to the peak voltage on capacitor 20 of integrator 21 during such cycles. Output counter 37 has counted from the baseline standard data presented by baseline thumbwheel switches 23 and the actual count contained therein at the completion of the measure cycle is reported as the sample concentration. The validity of the reported concentration is demonstrated in the mathematical model of FIG. 5A, as hereinafter described, and is further assured by operation of the blank channel compensation feature indicated by dotted lines C1' and C2'0 in FIG. 1A. Although ramping up in the presence of an altered baseline, as indicated by dashed line C1' produces a displacement in intercept on the vertical axis at $v'$, ramping down on a voltage proportional to altered baseline preserves the intercept on the horizontal axis, as indicated by dashed line C2'. The same procedure is effected cyclically with respect to each of the remaining flow cells, in turn, wherein the analytical results of each sample aliquot derived from a same sample can be displayed in correlated fashion, as described in U.S. Pat. No. 3,241,432.

Some chemistries require the use of a blank to compensate for variations in baseline or drift in light intensity. In the preferred embodiment, blank capabilities are provided for each of the analytical channels A–L by blank flow cells 3A–3L, respectively, Each blank flow cell 3A–3L effectively develops a voltage input to multiplexer 8, which routes such input to amplifier 10. The measurement sequences described above are the same, except that during time intervals T24–T25, dual slope control 18 instructs switch 11 along line 60 to connect the output of amplifier 10 to integrator 21 along contact 11c. As mentioned above and illustrated in FIG. 1A, ramping up along C1' due to an altered baseline or varied lamp intensity will be compensated by ramping down along C2' while the output of amplifier 10 is connected to integrator 21. The intercept on the horizontal axis is preserved, as shown in FIG. 1A, and the validity of the measurement is maintained. Where chemistries do not require a blank channel, the corresponding blank channel may be used nevertheless to compensate for intensity variations of lamp 4.

In the operation described above, an exponentially varying analytical system was linearized by introducing a scaled hyperbolic compensation. As well known, the variation in an analytical system can follow any one of many functions. For example, in the case of ion selective electrodes, the analytical signal varies logarithmically as a function of the concentration of the particular ion in the sample. In such event, the processing system can be linearized by compensating the logarithmically varying analytical signal with its inverse or first derivative function, i.e., with an exponential (antilog) compensation. Regardless of the compensation to be provided, the baseline cycle, effected during time period T1–T6, and the high-cal cycle, effected during time period T7–T15, are similar.

For example, and assuming that the input of integrator 21 is obtained from an ion selective electrode, capacitor 20 will be charged during the ramp-up cycle by a voltage related to the ionic concentration in the sample. To effect linearization, mode selector switch 58 is set by the operator to connect calibration rate multiplier 43 to the exponential rate multiplier 71. The state of the output counter 37 is fed back to exponential rate multiplier 71 via line 63, so as to continuously control such multiplier with the time-variable count contained therein. In effect, calibration rate multiplier 43, exponential rate multiplier 71 and output counter 37 combine to define the exponential sweep-frequency generator. However, for purposes of comparison with the above-described operation of hyperbolic sweep-frequency generator 45, the artifice of designating exponential rate multiplier 71 alone as the exponential sweep-frequency generator is adhered to.

Figure 6C:
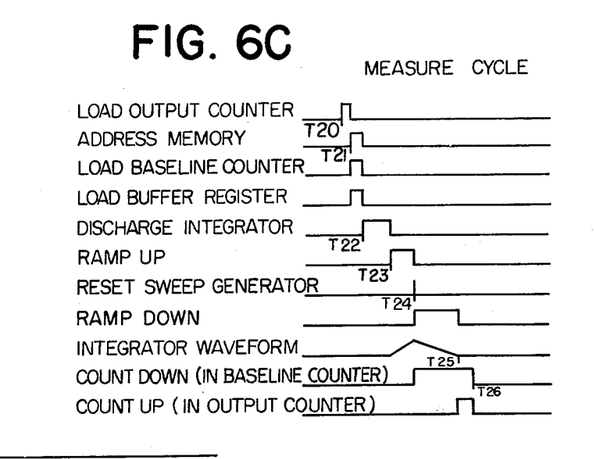

Referring again to the timing diagram of FIG. 6C and assuming that the baseline and calibration cycles have been completed, at time T20 channel address control 16 operates multiplexer 39 via line 17 to preset output counter 37 with the baseline concentration stored in baseline thumbwheel switches 23 at time T20. At time T21, cycle control 12 (1) enables line 69 to load the baseline word corresponding to the analytical channel, e.g. channel A, being analyzed into baseline counter 13 from memory 15 and (2) enables line 72 to clock the calibration word corresponding to such channel from memory 15 into buffer register 35, the memory being appropriately addressed by channel address control 16 and with the appropriate word address along line 30. Subsequently, at time T22–T23, dual slope control 18 operates switch 19 to discharge capacitor 20. At time T23, dual slope control 18 operates switch 11 along line 60 to connect integrator 21 via contact 11a to commence the ramp-up, or charging, of capacitor 20 as indicated by C1 in FIG. 1A. At this time, multiplexer 8 is appropriately addressed by channel address control 16 along line 17.

Since gate 55 is disabled during time period T23–T24, or ramp-up period, output counter 37 is not incremented (or decremented), the count remaining at the preset baseline concentration provided from baseline thumbwheel switches 23. At time T24, dual slope control 18 operates switch 11 along line 60 to connect integrator 21 via contact 11b to fixed reference $V_R$. During the time period T24–T25, or ramp-down period, the voltage across capacitor 20 is reduced to zero. Note: there is no reset of the exponential sweep-frequency generator at time T24 in FIG. 6C. At time T25, capacitor 20 has discharged, as indicated by C2 in FIG. 1A, and analog comparator 27 operates gate generator 48b to enable gate 55 to pass the train of pulses to output counter 37.

The measurement sequence is continued for each of the analytical channels A–L, in turn, cycle control 12 addressing each of multiplexers 8, 39, 41 and 67 and channel address control 16 and memory 15, so as to load the appropriate baseline word and calibration word into baseline counter 13 and buffer register 35, respectively. The analytical results are displayed and recorded in correlated fashion by output display device 62, which is strobed with appropriate phasing along line 70 by cycle control 12.

Figure 5B:
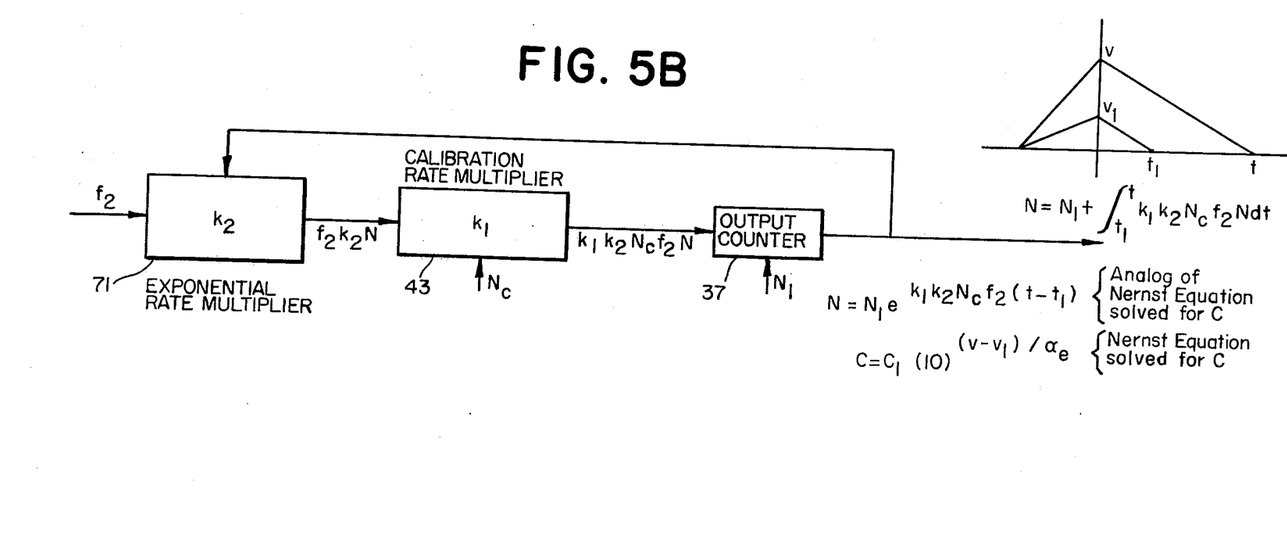

The colorimetric (logarithmic) mode and the electrode (antilogarithmic) mode are illustrated mathematically by FIGS. 5A and 5B, respectively. With respect to the colorimetric mode, the output frequency $f_2/(f_1 t)$ of hyperbolic sweep-frequency generator 45 varies hyperbolically with respect to time $t$ to effect linearization. For purposes of describing these mathematical illustrations, the following symbols are employed:

re: Calibration Standard No. 1
  $C_1$ Concentration
  $v_1$ Peak voltage across capacitor 20
  $t_1$ Time duration to crossover (T5–T6)
  $N_1$ Stored concentration data
re: Calibration Standard No. 2
  $C_2$ Concentration
  $v_2$ Peak voltage across capacitor 20
  $t_2$ Time duration to crossover (T11–T12)
  $N_2$ Stored concentration data
re: Sample
  C Concentration
  v Peak voltage across capacitor 20
  t Time duration to crossover (T24–T25)
  N Number equal to concentration of unknown
  $\alpha_c$ Property of colorimeter (product of absorptivity of medium and path length of flowcell)
  $\alpha_e$ Slope of electrode
  $k_1$ Constant of proportionality for calibration rate multiplier 43
  $k_2$ Constant of proportionality of exponential rate multiplier 71
  $N_c$ Control number of calibration rate multiplier 43
  e Base of natural logarithms
  $f_1$ constant frequency input to up-counter 48a
  $f_2$ Constant frequency input to down-counter 47 or exponential rate multiplier 71

During the time interval T25–T26, as described, the total count N in output counter 37 is given by the equation labeled "analog of Beer's Law solved for c" in FIG. 5A and indicates the concentration of the particular constituent under analysis. As described, geometrically related changes in the output voltage of amplifier 9 correspond to linearly related changes in concentration, according to Beer's Law. Accordingly, the logarithmically varying count in output counter 37, when properly scaled, provides appropriate linearization of the analytical signal.

The measurement cycle, for example, when ion specific electrodes are used, is essentially similar. As described, linearly related changes in the output voltage of amplifier 9 correspond to geometrically related changes in the concentration of the ionic constituent in the sample. To linearize such analytical signal, the mode selector switch 58 is operated to connect the exponential rate multiplier 71 to calibration rate multiplier 43, such that the frequency of the train of pulses to be passed through gate 55 increases exponentially as a function of time, by virtue of the feedback along lead 63. In such operation, the frequency has been scaled according to the calibration word stored in buffer register 35. Accordingly, the output frequency of the calibration rate multiplier 43 and, hence, the count in output counter 37 exhibits a geometric growth as a function of time. The total count N present in output counter 37 during time interval T25–T26 of any measurement cycle is given by the equation labeled "Analog of Nernst Equation Solved for C" in FIG. 5B. Exponential rate multiplier 71 is controlled by the increasing (or decreasing) count in output counter 37, so as to control the output frequency as an increasing (or decreasing) function of time. Accordingly, the output frequency from the calibration rate multiplier 43 exhibits a geometric growth as hereinafter demonstrated.

Accordingly, the number of pulses per unit time from calibration rate multiplier 43 continuously increases in exponential fashion, such that the count in the output counter also increases exponentially, whereby linearization is achieved. Such linearization is achieved, by virtue of output counter 37 functioning as an accumulator or integrator of the output pulses from calibration rate multiplier 43. Since the integral of an exponential function is also an exponential function, the count in the output counter 37 compensates for the non-linear electrode output and provides system outputs linear with and equal to the concentrations of the ionic constituents.

Starting at time T25, pulses passing from calibration rate multiplier 43 are counted by output counter 37. Since the exponential sweep frequency generator (exponential rate multiplier 71) is continuously controlled along line 63 with the instantaneous count in output counter 37, which is now continuously increasing, the output frequency of the exponential frequency sweep generator also increases exponentially as a function of time. The count in the output counter 37 increases exponentially as a function of time as a result of its counting (integrating) an exponentially varying time function of frequency.

As described, equal increments in the electrode output voltage correspond to equal factors of change in concentration, according to the Nernst formulation. Accordingly, the exponentially varying count in output counter 37 provides appropriate linearization to the analytical signal, since it increments by equal factors during equal intervals of time, as translated from the equal increments of electrode output voltage by dual-slope integrator 21. Hence, such linearization provides a count in output counter 37 which indicates directly the concentration of the constituent in the sample under analysis.

It is apparent that any signal which varies non-linearly with respect to concentration of constituent under analysis, can be compensated by generating the appropriate time varying function of frequency. Regardless of the manner in which the analytical signal varies, the frequency of the pulses to be counted can be varied according to this function, such that the number of pulses provided during the time gate T25–T26, which is the translation of the analytical signal into a time referenced duration, would indicate directly the concentration increase above baseline or, with baseline summed in (preset), then would indicate the concentration per se. In the exponential mode just described, the baseline concentration must be preset into the output counter 37 for the process to function, as inspection of FIG. 5B will indicate.

In certain system applications employing transducers having linear characteristics, e.g., spectrophotometers, pH electrodes, polarographic electrodes, etc., fixed frequency $f_2$ generated by clock oscillator 26 is applied along line 59 to the mode selector switch 58 which routes it to the input of calibration rate multiplier 43. Because of this introduction of fixed frequency $f_2$, in place of either the varying frequency from hyperbolic frequency sweep generator 45 or the varying frequency from exponential rate multiplier 71, the system exhibits a linear characteristic and provides for two point standardization.

In justification of the qualitative description given above, the following quantitative description is given. Either Beer's law as formulated by the equation $$v = v_1(10)^{-\alpha_c(C - C_1)} \qquad 1.$$

or the Nernst equation as formulated by the equation $$v = v_1 + \alpha_e \log(C/C_1)$$

are solved, below, for the unknown concentration, C, of the sample as a function of the voltage, $v$, produced by the sample. The respective solutions to these equations are given by equations $$C = C_1 + (1/\alpha_e)\log(v_1/v), \text{ and} \qquad 3.$$

$$C = C_1(10)^{(v-v_1)/\alpha_e} \qquad 4.$$

The apparatus described above functions in part as a form of analog computer which is initialized during its internal automatic standardization procedure, as described. This "analog" computer is described in FIG. 5A and FIG. 5B by functional blocks and implements equations analogous to equations (3) and (4). Thus, instead of providing concentration, C, as a function of voltage, $v$, it provides instead a number, N, as a function of time, $t$. Consequently, the number, N, must be equal to the concentration, C, which is indeed the case after suitable constraint by the automatic standardization procedure and after the subsequent measurement cycle has been concluded.

The analog of equation (3) which is the solution to the formulation of Beer's law is given by:

$$N = N_1 + (k_1 N_c f_2/f_1)\ln(t_1/t) \qquad 5.$$

The analog of equation (4) which is the solution to the Nernst equation is given:

$$N = N_1 e^{k_1 k_2 N_c f_2 (t - t_1)} \qquad 6.$$

The equivalance of equations (5) and (6) to equations (3) and (4) respectively is guaranteed by the geometry of similar triangles as demonstrated in FIG. 5A and FIG. 5B respectively. Consequently, integrator 21 converts $v_1/v$ into $t_1/t$ and alternately converts $(v - V_1)$ into $(t - t_1)$ and, by previous suitable selection of $N_c$ by successive approximations, thus makes the reported number, N, numerically equal to the concentration, C, of the constituent.

The analog equations (5) and (6) were obtained as solutions to equations:

$$N = N_1 + \int_t^{t_1} (K_1 N_c f_2/f_1)(1/t)dt \qquad (7)$$

and $$N = N_1 + \int_{t_1}^t k_1 k_2 N_c f_2 N dt \qquad (8)$$

Equations (7) and (8) describe the signal processing portion of the apparatus, as depicted in FIG. 5A and FIG. 5B, respectively, for compensating for the nonlinearity of the formulations respectively of Beer's Law and the Nernst equation.

Thus, equations (7) and (8) are also analogs of equations (3) and (4), respectively, and permit the overall system apparatus described above to report a number, N, equal to the unknown concentration, C. This is done in turn for each constituent of interest in the sample.

What is claimed is:

1. Apparatus for processing signals comprising means for analyzing fluid samples for the concentration of a particular constituent and for obtaining resulting analytical signals, each of said signals varying as a function of the concentration of said constituent in each sample, means for calibrating said apparatus on a two point basis, said calibrating means comprising reversible counter means for producing a time reference corresponding to the response of said apparatus to a first calibration standard of known concentration, said calibration means further including means for comparing by a successive approximation algorithm the response of said apparatus to the known concentration of a second calibration standard, said comparing means including means for presenting the known concentration of said second calibration standard to a digital comparator for iterative comparison with successive responses of said analyzing means to said second concentration standard so as to derive a control word, means including an A/D converter means comprising a dual-slope integrator for converting each of said analytical signals corresponding to said samples to a proportional time duration, means for generating the first derivative function of said varying function, and processing means for linearizing and scaling each of said analytical signals according to said derivative function, said corresponding time duration, said time reference and said control word.

2. Apparatus as in claim 1, wherein said analyzing means further includes a colorimeter, whereby the analytical signal varies exponentially with concentration, and said generating means being operative to generate a logarithmic linearizing function.

3. Apparatus as in claim 2, wherein said generating means includes a hyperbolic frequency sweep generator and output counter means responsive to said hyperbolic frequency sweep generator for developing a digital output equal to the concentration of said constituent in a particular fluid sample.

4. Apparatus as in claim 3 wherein said output counter is connected through a gating arrangement to said hyperbolic frequency sweep generator, and means for enabling said gating arrangement for a time interval equal to the difference between said time reference and said time duration corresponding to the analytical signal being analyzed.

5. Apparatus as in claim 1, wherein the analytical signal varies linearly with concentration, and said generating being operative to generate a linear function.

6. Apparatus as in claim 4, wherein said hyperbolic frequency sweep generator comprises a down-counter and an up-counter, a source of pulses of first frequency connected to said down-counter, a source of pulses of second frequency connected to said up-counter, said first frequency being greater than said second frequency, and means for presetting the down-counter with the count of said up-counter upon said down-counter reaching the zero state.

7. Apparatus as in claim 6, wherein said source of first frequency pulses is an oscillator and said source of second frequency pulses is a frequency divider arrangement connected between said oscillator and said up-counter.

8. Apparatus as in claim 7, wherein said generating means includes a constant frequency generator and output counter means responsive to said constant frequency generator for developing a digital output equal to the concentration of said constituent in a particular fluid sample.

9. Apparatus as in claim 3, further including means for multiplying the output of said hyperbolic frequency sweep generator to scale said digital output developed by said output counter means.

10. Apparatus as in claim 9, further including means responsive to said calibration means for controlling said multiplying means according to said control word.

11. Apparatus according to claim 9, wherein said calibration means further includes means for comparing by a successive approximation algorithm the response of said analytical system to the known concentration of said second calibration standard, comparative means for relating the difference in the response of said analytical system to said first and second standards to the difference between said known concentrations of said first and second standards, means responsive to said comparative means to produce a control word, said multiplying means being responsive to said last-mentioned means according to said control word to modify said digital output, so as to equate said differences, whereby two point calibration of said analytical system is effected.

12. Apparatus as in claim 1, wherein said analyzing means further includes an ion selective electrode, whereby the analytical signal varies logarithmically with concentration, and said generating means being operative to generate an exponential linearizing function.

13. Apparatus as in claim 12 wherein said generating means includes an exponential frequency sweep generator, means for multiplying the output of said exponential frequency sweep generator to scale said linearizing function, and output counter means for counting the output of said multiplying means for developing a digital output equal to the concentration of said constituent in a particular fluid sample.

14. Apparatus as in claim 13 wherein said output counter is connected through a gating arrangement to said exponential frequency sweep generator, and means for enabling said gating arrangement for a time interval equal to the difference between said time reference and said time duration corresponding to the analytical signal being analyzed.

15. Apparatus as in claim 13, further including means responsive to said calibration means for controlling said multiplying means according to said control word.

16. Apparatus according to claim 13, wherein said calibration means further includes means for comparing by a successive approximation algorithm the response of said analytical system to the known concentration of said second calibration standard, comparative means for relating the ratio of the response of said analytical system to said first and second standards to the ratio of the known concentrations of said first and second standards, means responsive to said comparative means to produce a control word, said multiplying means being responsive to said last-mentioned means according to said control word to modify said digital output so as to equate said ratios, whereby two point calibration of said analytical system is effected.

17. Apparatus as in claim 1, wherein said analyzing means further includes means for passing said samples successively as a continuous stream and means for treating each of said samples, in turn, for said constituent.

18. Apparatus as in claim 1, wherein said analyzing means includes a plurality of analytical channels, each of said analytical channels being operative to analyze said sample for a different selected constituent of interest, said analyzing means further including means for dividing said sample between said analytical channels, said calibrating means being operative to produce a time reference with respect to each of said analytical channels, said converting means being operative to convert the analytical signal from each analytical channel to a proportional time duration, said processing means being operative with respect to each of said analytical channels.

19. Apparatus as in claim 18, further including a random access memory for storing time references produced for each of said analytical channels, and means for addressing said memory according to a particular analytical channel.

20. Apparatus as in claim 18, wherein said calibration means further includes means for comparing by a successive approximation algorithm the response of each of said analytical channels to the known concentration of an appropriate second calibration standard, so as to derive a control word for each of said analytical channels, said processing means being operative according to the control word derived for each of said analytical channels.

21. Apparatus as in claim 20, further including a random access memory for storing control words derived for each of said analytical channels, and means for addressing said memory according to a particular analytical channel.

22. Apparatus as in claim 18, wherein said analyzing means further includes one or more blank channels for generating blank signals and means for referencing selected ones of said analytical signals to selected ones of such blank signals.

23. Apparatus as in claim 18, further including multiplexing means for selectively connecting said analytical channels to said processing means.

24. Apparatus as in claim 1, wherein said analyzing means includes a blank channel for producing a voltage reference, and means for connecting said dual-slope integrator to said voltage reference during ramp-down of said dual-slope integrator.

25. Apparatus as in claim 1, wherein said analytical signals are analog, and further including means for directly converting each of said analytical signals from a non-linear analog signal to a linear digital output.

* * * * *